United States Patent
Oh et al.

(10) Patent No.: US 12,110,539 B2
(45) Date of Patent: Oct. 8, 2024

(54) METAL ION-START DNA POLYMERASE SWITCH AND ISOTHERMAL POLYMERASE AMPLIFICATION METHOD USING THE SAME

(71) Applicant: POSTECH Research and Business Development Foundation, Pohang-si (KR)

(72) Inventors: Seung Soo Oh, Pohang-si (KR); Hye Bin Yoo, Yongin-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 236 days.

(21) Appl. No.: 17/675,229

(22) Filed: Feb. 18, 2022

(65) Prior Publication Data
US 2023/0074735 A1 Mar. 9, 2023

(30) Foreign Application Priority Data
Sep. 9, 2021 (KR) .................. 10-2021-0120489

(51) Int. Cl.
 *C12Q 1/6823* (2018.01)
 *C12Q 1/6853* (2018.01)
 *C12Q 1/686* (2018.01)
(52) U.S. Cl.
 CPC ......... *C12Q 1/6823* (2013.01); *C12Q 1/6853* (2013.01); *C12Q 1/686* (2013.01)
(58) Field of Classification Search
 CPC ........... C12Q 1/6823; C12Q 1/53; C12Q 1/06
 See application file for complete search history.

(56) References Cited

U.S. PATENT DOCUMENTS 10,604,796 B2 * 3/2020 Dong ..................... C12P 19/34

FOREIGN PATENT DOCUMENTS

WO WO-2021206635 A1 * 10/2021 ........... C12N 9/1252

OTHER PUBLICATIONS

Dang C, Jayasena SD. Oligonucleotide inhibitors of Taq DNA polymerase facilitate detection of low copy No. targets by PCR. J Mol Biol. Nov. 29, 1996;264(2):268-78. doi: 10.1006/jmbi.1996.0640. PMID: 8951376. (Year: 1996).*
Yun Lin, Sumedha D Jayasena, Inhibition of multiple thermostable DNA polymerases by a heterodimeric aptamer1 1Edited by D. E. Draper, Journal of Molecular Biology, vol. 271, Issue 1, (Year: 1997).*
Gening LV, Klincheva SA, Reshetnjak A, Grollman AP, Miller H. RNA aptamers selected against DNA polymerase beta inhibit the polymerase activities of DNA polymerases beta and kappa. Nucleic Acids Res. May 17, 2006;34(9):2579-86. doi: 10.1093/nar/gkl326. PMID: 16707660; PMCID: PMC1463896. (Year: 2006).*
Ewa Kowalska, Filip Bartnicki, Ryo Fujisawa, Piotr Bonarek, Paweł Hermanowicz, Toshiki Tsurimoto, Klaudia Muszyńska, Wojciech Strzalka, Inhibition of DNA replication by an anti-PCNA aptamer/PCNA complex, Nucleic Acids Research, vol. 46, Issue 1, Jan. 9, 2018, pp. 25-41 (Year: 2017).*
Lakhin AV, Kazakov AA, Makarova AV, Pavlov YI, Efremova AS, Shram SI, Tarantul VZ, Gening LV. Isolation and characterization of high affinity aptamers against DNA polymerase iota. Nucleic Acid Ther. Feb. 2012;22(1):49-57. doi: 10.1089/nat.2011.0324. Epub Jan. 5, 2012. PMID: 22221258. (Year: 2012).*
Zhu C, Wen Y, Li D, Wang L, Song S, Fan C, Willner I. Inhibition of the in vitro replication of DNA by an aptamer-protein complex in an autonomous DNA machine. Chemistry. Nov. 9, 2009;15(44):11898-903. doi: 10.1002/chem.200901275. PMID: 19777511. (Year: 2009).*
New England Biolabs Hot Start Taq M0495S Product Specification Sheet (Year: 2015).*
New England Biolabs Bst Warmstart DNA polymerase M0538M Product Specification Sheet (Year: 2016).*
New England BioLabs Q5 Hifi DNA polymerase M0493S/L product specification (Year: 2015).*
Alexander V. Sidorov, Jane A. Grasby, David M. Williams, Sequence-specific cleavage of RNA in the absence of divalent metal ions by a DNAzyme incorporating imidazolyl and amino functionalities, Nucleic Acids Research, vol. 32, Issue 4, Feb. 15, 2004, pp. 1591-1601, (Year: 2004).*
Roth A, Breaker RR. An amino acid as a cofactor for a catalytic polynucleotide. Proc Natl Acad Sci U S A. May 26, 1998;95(11):6027-31. doi: 10.1073/pnas.95.11.6027. PMID: 9600911; PMCID: PMC27579. (Year: 1998).*
Sidorov AV, Grasby JA, Williams DM. Sequence-specific cleavage of RNA in the absence of divalent metal ions by a DNAzyme incorporating imidazolyl and amino functionalities. Nucleic Acids Res. Mar. 5, 2004;32(4):1591-601. doi: 10.1093/nar/gkh326. PMID: 15004246; PMCID: PMC390309. (Year: 2004).*
A Colorimetric Lead Biosensor Using DNAzyme-Directed Assembly of Gold Nanoparticles Juewen Liu and Yi Lu Journal of the American Chemical Society 2003 125 (22), 6642-6643 DOI: 10.1021/ja034775u (Year: 2003).*

(Continued)

*Primary Examiner* — Neil P Hammell
*Assistant Examiner* — Amanda M Zahorik
(74) *Attorney, Agent, or Firm* — LEX IP MEISTER, PLLC (57) ABSTRACT

The present invention relates to a metal ion-start DNA polymerase switch, a composition for isothermal polymerase amplification containing the same, and an isothermal amplification method using the metal ion-start DNA polymerase switch. The metal ion-start DNA polymerase switch according to the present invention may comprise: a binding module composed of TQ30 aptamer; a locking or unlocking module; and a catalytic module connecting between the binding module and the locking or unlocking module and composed of DNAzyme.

5 Claims, 9 Drawing Sheets

Specification includes a Sequence Listing.

(56) References Cited

OTHER PUBLICATIONS

John C. Achenbach, Razvan Nutiu, Yingfu Li, Structure-switching allosteric deoxyribozymes, Analytica Chimica Acta, vol. 534, Issue 1, (Year: 2004).*

Walter JG, Stahl F. Aptazymes: Expanding the Specificity of Natural Catalytic Nucleic Acids by Application of In Vitro Selected Oligonucleotides. Adv Biochem Eng Biotechnol. 2020;170:107-119. doi: 10.1007/10_2019_92. PMID: 30847536. (Year: 2020).*

"Aptamer." Merriam-Webster.com Medical Dictionary, Merriam-Webster, https://www.merriam-webster.com/medical/aptamer. Accessed Dec. 13, 2023. (Year: 2023).*

"Lock." Merriam-Webster.com Dictionary, Merriam-Webster, https://www.merriam-webster.com/dictionary/lock. Accessed Dec. 13, 2023. (Year: 2023).*

Garcia-Diaz M, Bebenek K. Multiple functions of DNA polymerases. CRC Crit Rev Plant Sci. Mar. 2007;26(2): 105-122. doi: 10.1080/07352680701252817. PMID: 18496613; PMCID: PMC2391090. (Year: 2007).*

Sharkey, D., Scalice, E., Christy, K. et al. Antibodies as Thermolabile Switches: High Temperature Triggering for the Polymerase Chain Reaction. Nat Biotechnol 12, 506-509 (1994). https://doi.org/10.1038/nbt0594-506 (Year: 1994).*

Zhaojuan Zhou, Lu Xiao, Yu Xiang, Jun Zhou, Aijun Tong, A general approach for rational design of fluorescent DNA aptazyme sensors based on target-induced unfolding of DNA hairpins, Analytica Chimica Acta, vol. 889, 2015, pp. 179-186, ISSN 0003-2670, https://doi.org/10.1016/j.aca.2015.06.036. (Year: 2015).*

Chinh Dang et al., "Oligonucleotide Inhibitors of Taq DNA Polymerase Facilitate Detection of Low Copy Number Targets by PCR", J. Mol. Biol. (1996) 264, 268-278.

Runjhun Saran et al., "A comparison of two classic Pb2+-dependent RNA-cleaving DNAzymes", Inorg. Chem. Front., 2016, 3, 494-501, Jan. 11, 2016, DOI: 10.1039/c5qi00125k.

Ki Soo Park et al., "Metal ion triggers for reversible switching of DNA polymerase", Chem. Commun., 2016, 52, 4868-4871, Feb. 17, 2016, DOI: 10.1039/c6cc00454g.

Ki Soo Park et al., "Target DNA induced switches of DNA polymerase activity", Chem. Commun., 2015, 51, 9942-9945, Apr. 30, 2015, DOI: 10.1039/c5cc02060c.

* cited by examiner

SEQUENCE LISTING

```
<160> NUMBER OF SEQ ID NOS: 8

<210> SEQ ID NO 1
<211> LENGTH: 69
<212> TYPE: DNA
<213> ORGANISM: Artificial Sequence
<220> FEATURE:
<223> OTHER INFORMATION: DNAzymatic switch

<400> SEQUENCE: 1
gagtccaata ggaagagtcc aatgtacagt attggactct gaagtagcgc cgccgtattg      60
gactcttcc                                                              69

<210> SEQ ID NO 2
<211> LENGTH: 71
<212> TYPE: DNA
<213> ORGANISM: Artificial Sequence
<220> FEATURE:
<223> OTHER INFORMATION: DNAzymatic switch

<400> SEQUENCE: 2
gcggcgtcac tataggaaga tccaatgtac agtattggat ctgaagtagc gccgccgtat      60
agtgacgccg c                                                           71

<210> SEQ ID NO 3
<211> LENGTH: 58
<212> TYPE: DNA
<213> ORGANISM: Artificial Sequence
<220> FEATURE:
```

<223> OTHER INFORMATION: DNAzymatic switch

<400> SEQUENCE: 3
aagacaatag gaagacaatg tacagtattg tctgaagtag cgccgccgta ttgtcttc    58

<210> SEQ ID NO 4
<211> LENGTH: 64
<212> TYPE: DNA
<213> ORGANISM: Artificial Sequence
<220> FEATURE:
<223> OTHER INFORMATION: DNAzymatic switch

<400> SEQUENCE: 4
ctgtacattg taggaagagc tttgctctga agtagcgccg ccgtacaatg tacagtattg    60
tacg    64

<210> SEQ ID NO 5
<211> LENGTH: 67
<212> TYPE: DNA
<213> ORGANISM: Artificial Sequence
<220> FEATURE:
<223> OTHER INFORMATION: DNAzymatic switch

<400> SEQUENCE: 5
ctgtacatta ctaggaagag ctttgctctg aagtagcgcc gccgtagtaa tgtacagtat    60
tactacg    67

<210> SEQ ID NO 6
<211> LENGTH: 65
<212> TYPE: DNA
<213> ORGANISM: Artificial Sequence
<220> FEATURE:
<223> OTHER INFORMATION: DNAzymatic switch

<400> SEQUENCE: 6
cgtaatactg tacattagga agagctttgc tctgaagtag cgccgccgta atgtacagta    60
ttacg    65

<210> SEQ ID NO 7
<211> LENGTH: 59
<212> TYPE: DNA
<213> ORGANISM: Artificial Sequence
<220> FEATURE:
<223> OTHER INFORMATION: DNAzymatic switch

<400> SEQUENCE: 7
ggaagagtcc aatgtacagt attggactct gaagtagcgc cgccgtattg gactcttcc    59

<210> SEQ ID NO 8
<211> LENGTH: 52
<212> TYPE: DNA
<213> ORGANISM: Artificial Sequence
<220> FEATURE:
<223> OTHER INFORMATION: DNAzymatic switch

<400> SEQUENCE: 8
ggaagagctt tgctctgaag tagcgccgcc gtacaatgta cagtattgta cg    52

METAL ION-START DNA POLYMERASE SWITCH AND ISOTHERMAL POLYMERASE AMPLIFICATION METHOD USING THE SAME

BACKGROUND

1. Technical Field

The present invention relates to a metal ion-start DNA polymerase switch, a composition for isothermal polymerase amplification containing the same, and an isothermal polymerase amplification method using the metal ion-start DNA polymerase switch.

2. Related Art

As DNA polymerases are active even at ambient temperature, nonspecific amplification of DNA in polymerase chain reaction (PCR) inevitably occurs (Coleman and Tsongalis 2017; Eckert and Kunkel 1991). Before initiating a thermocycling process for polymerase chain reaction (PCR), the active polymerases are capable of extending PCR primers even if the specifically designed primers are bound to non-target strands with incomplete homology. This nonspecific amplification seriously reduces the detection accuracy of target amplicons, and thus it has been a critical issue in quantitative assays, such as real-time PCR (RT-PCR) (Bustin and Nolan 2004; Chou et al. 1992; Kramer and Coen 2001).

To overcome this problem, a heat-based polymerase activation technique, called hot-start PCR, has been developed and widely used for diverse diagnostic applications (Birch et al. 1996; Green and Sambrook 2018; Paul et al. 2010). Due to the specific binding between DNA polymerases and their inhibitors (e.g., antibodies and aptamers), the DNA-copying enzymes can be effectively deactivated, thereby preventing the formation of undesired products at ambient temperature. Interestingly, simple temperature elevation can induce the inhibitors to be spontaneously dissociated from the polymerases, and thus the activated enzymes become ready to perform amplification reactions highly specific for pre-defined gene targets. In this way, the hot-start PCR excludes the possibility of false-positive detection, achieving elaborate quantitative determination of nucleic acid analytes for actual clinical samples (Dang and Jayasena 1996; Lin and Jayasena 1997; Scalice et al. 1994; Sharkey et al. 1994).

However, the hot-start control of DNA polymerases would not be attractive for point-of-care (PoC) systems. Thermocyclers are required for polymerase activation and analyte amplification, even though simple and instrument-free techniques are preferred for in-field detection (Lee 2017; Marx 2015). For this reason, isothermal amplification (e.g., rolling circle amplification (RCA) and loop-mediated isothermal amplification (LAMP)) attracts a lot of attention nowadays, because it holds the great potential to rapidly cope with infectious diseases, including coronavirus infection disease (COVID-19), in the right place at the right time (Hsieh et al. 2012; Song et al. 2016). However, this isothermal amplification-based analyte detection is inherently qualitative, not quantitative. During the spontaneous and continuous amplification process, it is difficult to specifically designate the start and end points of amplification reactions. Without controlling their reaction time and conditions, the one-by-one amplicon detection is likely to be qualitative by comparing the amplification result only with positive and negative controls. Like as thermocycling amplification has been effectively controlled by heat activation, isothermal amplification would require a specific reaction controller allowing PoC tests to be reliable and quantitative, even as performed in a parallel manner.

SUMMARY

To solve the above-described problems, the present inventors have developed a metal ion-start isothermal amplification technique capable of effectively controlling activation or deactivation of DNA polymerase at room temperature.

An object of the present invention is to provide a metal ion-start DNA polymerase switch for isothermal amplification and a composition for isothermal polymerase amplification containing the same, which may be widely applied in point-of-care (PoC) tests.

Another object of the present invention is to provide a method of isothermally amplifying a target gene using the composition for isothermal polymerase amplification and metal ions.

To achieve the above objects, the present invention provides a metal ion-start DNA polymerase switch comprising: a binding module composed of an aptamer for inhibiting DNA polymerase activity; a locking or unlocking module; and a catalytic module connecting between the binding module and the locking or unlocking module and composed of DNAzyme.

Preferably, the DNAzyme may be selected from among $Pb^{2+}$-responsive and RNA-cleaving GR5 DNAzyme, $Na^+$-responsive NaA43 DNAzyme, $Cu^{2+}$-responsive PSCu10 DNAzyme, $Ca^{2+}$-responsive EtNa DNAzyme, $Ln^{3+}$-responsive Dy10a, and other DNAzymes.

Preferably, the metal ion-start DNA polymerase switch comprising the locking module may comprise a nucleic acid sequence selected from the group consisting of SEQ ID NOs: 1 to 3.

Preferably, the metal ion-start DNA polymerase switch comprising the unlocking module may comprise a nucleic acid sequence selected from the group consisting of SEQ ID NOs: 4 to 6.

The present invention also provides a composition for isothermal polymerase amplification containing the metal ion-start DNA polymerase switch and a DNA polymerase.

Preferably, the metal ion-start DNA polymerase switch comprising the locking module may be configured to activate the DNA polymerase by binding of the binding module to the DNA polymerase in the presence of metal ions.

Preferably, the metal ion-start DNA polymerase switch comprising the unlocking module may be configured to deactivate the DNA polymerase by binding of the binding module to the DNA polymerase in the presence of metal ions.

The present invention also provides an isothermal amplification method comprising steps of: preparing a mixture by mixing the metal ion-start DNA polymerase switch, metal ions, and a sample to be analyzed, and heating and incubating the mixture; preparing a composition for isothermal polymerase amplification by adding a DNA polymerase to the incubated mixture, followed by incubation; and isothermally amplifying a target gene using a mixture obtained by mixing a solution containing target gene-start primers and a template with the composition for isothermal polymerase amplification.

The present invention also provides a method for quantitative analysis of a target gene comprising steps of: preparing a mixture by mixing the metal ion-start DNA polymerase switch, metal ions, and a sample to be analyzed, and heating and incubating the mixture; and quantifying the amount of the target gene in the sample using a portable UV lamp and a smartphone camera.

The effects of the present invention are as follows. Using the metal ion-start DNA polymerase switch according to the present invention, a plurality of isothermal amplification reactions can be initiated and terminated at the same time, and the same reaction conditions for samples may be formed, and thus it is possible to quantitatively analyze and compare multiple samples. In addition, it is possible to quantify the amounts of genes in human serum and saliva at a low detection limit by using a portable UV lamp and a smartphone camera. Therefore, it is expected that the isothermal amplification systems in PoC tests that are performed in actual fields can be effectively controlled using the metal ion-start DNA polymerase switch according to the present invention without a complicated sample purification process.

BRIEF DESCRIPTION OF THE DRAWINGS

FIGS. 1a and 1b schematically show lead ion ($Pb^{2+}$)-start DNA polymerase switches which are metal ion-start DNA polymerase switches according to the present invention.

DETAILED DESCRIPTION

The present invention relates to a metal ion-start DNA polymerase switch, a composition for isothermal polymerase amplification containing the same, and an isothermal polymerase amplification method using the metal ion-start DNA polymerase switch.

According to one embodiment of the present invention, the metal ion-start DNA polymerase switch comprises: a binding module; a locking or unlocking module; and a catalytic module composed of DNAzyme.

Hereinafter, the present invention will be described in detail with reference to the accompanying drawings.

Figure 1A:
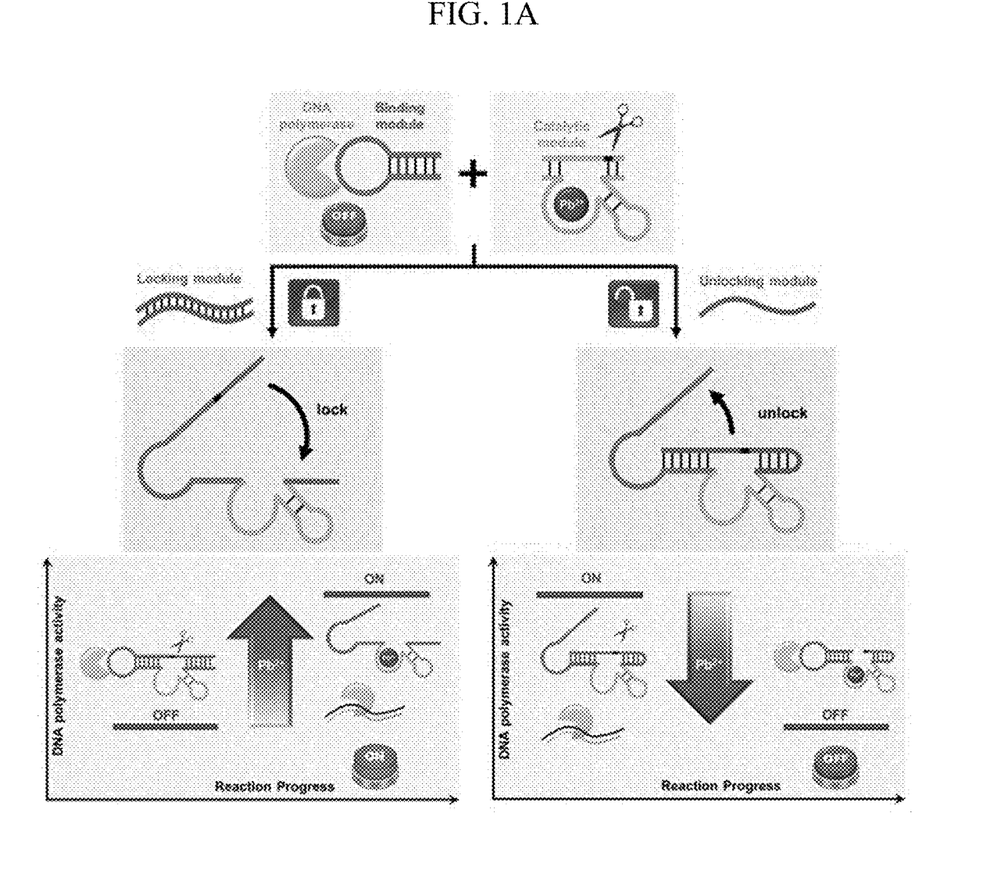
FIG. 1a shows the structure and operating principle of the lead ion-start DNA polymerase switches according to the present invention.
Figure 1B:
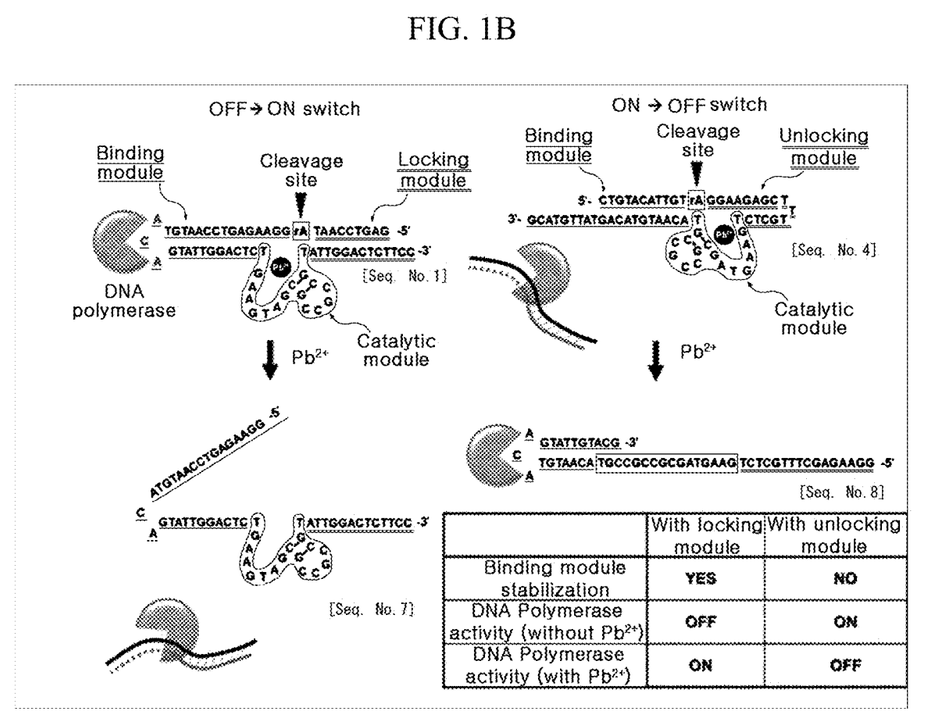
FIG. 1b shows modular designs of the lead ion-start DNA polymerase switches according to the present invention.

FIG. 1 schematically shows the metal ion-start DNA polymerase switch according to the present invention. The metal ion-start DNA polymerase switch according to the present invention is composed of three functional modules: a binding module; a catalytic module; and a locking or unlocking module.

As the binding module, an aptamer that inhibits DNA polymerase activity may be used. For example, a hairpin-shaped TQ30 aptamer that can inhibit the activity of Taq DNA polymerase may be used (Dang and Jayasena 1996; Ho et al. 2018; Lin and Jayasena 1997; Park et al. 2016a; Park et al. 2015, 2016b). Specifically, this TQ30 aptamer is composed of: a fixed loop that directly contacts the DNA polymerase; and a programmable stem that serves as a binding stabilizer. In addition to the TQ30 aptamer, a TQ21 aptamer that inhibits Tth polymerase activity may also be used. Additionally, other binding modules may also be used to control the activities of various enzymes other than the DNA polymerase.

The catalytic module that is used in the present invention may be selected from among GR5 DNAzyme, which is a classic $Pb^{2+}$-dependent, RNA-cleaving DNAzyme, that displays an exceptionally high selectivity to $Pb^{2+}$ targets (Saran and Liu 2016), $Na^+$ ion-responsive NaA43 DNAzyme, $Cu^{2+}$ ion-responsive PSCu10 DNAzyme, $Ca^{2+}$ ion-responsive EtNa DNAzyme, $Ln^{3+}$-responsive Dy10a, and the like. In addition, any DNAzyme capable of causing cleavage in response to ions may also be used. This module composed of GR5 DNAzyme provides a $Pb^{2+}$ recognition site for the molecular switch of the present invention, which eventually undergoes a dynamic conformation change as a result of $Pb^{2+}$-triggered RNA cleavage.

In addition, a faster reaction can be induced using a non-catalytic module, which can also be applied to real-time detection. For example, an aptamer that causes a large structural change instead of cleavage may be used, and as an example, a switch responsive to K+ may be constructed using a G-quadruplex nanostructure. As another example, using a structure-switching aptamer such as an ATP aptamer, it is possible to construct a switch that responds not only to ions but also to small molecules such as ATP.

Finally, the locking or unlocking module is included as a key component that determines activation or deactivation of DNA polymerases in response to a metal ion such as $Pb^{2+}$.

As the three modules are systematically correlated with each other, the lead ion-start switch of the present invention behaves as an elaborate nanomachine, allowing bidirectional control of DNA polymerase activity initiated by metal ion addition.

Relying on the choice between the locking module and the unlocking module, it is possible to switch from deactivation (OFF state) to activation (ON state) of DNA polymerase and vice versa (FIG. 1a). When the locking module is installed into the molecular switch (OFF→ON switch, left), its response to $Pb^{2+}$ is defined to activate the DNA polymerase. Specifically, in the absence of $Pb^{2+}$, the OFF→ON switch is structurally locked to have the stable binding module, which can strongly bind to the DNA polymerase for hibernation. However, in the presence of $Pb^{2+}$, $Pb^{2+}$-triggered RNA cleavage within the catalytic module causes to destabilize the locked structure and subsequently liberate the DNA-copying enzyme, so that the reaction of DNA amplification becomes active.

On the other hand, the molecular switch equipped with the unlocking module (ON→OFF switch, right) responds to $Pb^{2+}$ in the opposite manner. That is, the unlocking module disturbs the stable formation of the binding module, but upon $Pb^{2+}$ addition, the cleavage of the catalytic module permits the structural reorganization of the molecular switch, making the binding module to suppress the primer extension of the DNA polymerase.

The metal ion-start switch was rationally constructed as the three functional modules were systematically integrated with one another (FIG. 1b).

In addition, according to one embodiment of the present invention, not only Taq DNA polymerase but also various types of DNA polymerase can be controlled in the same manner. This is possible through replacement of the aptamer module. Various polymerase inhibitory aptamers suitable for isothermal amplification can be newly discovered with the help of in vitro selection technology. For example, transcription of T7 RNA polymerase may be controlled in the same manner by using an RNA aptamer. Furthermore, the system of the present invention may also be applied to control the activities of various biological enzymes in addition to DNA polymerase. The activities of various enzymes can be controlled in the same manner only through replacement of the aptamer module.

Table 1 below shows the DNA sequences (5'→3') of the OFF→ON switches among the lead ion-start switches comprising the locking module according to one embodiment of the present invention. In Table 1, rA signifies an RNA nucleotide.

TABLE 1

| Name | DNA sequence (5'→3') |
| --- | --- |
| OFF→ON switch (optimal locking) | 5'-GAGTCCAATrAGGAAGAGTCCAATGTACAGT ATTGGACTCTGAAGTAGCGCCGCCGTATTGGACT CTTCC-3' (SEQ ID NO: 1) |
| OFF→OFF switch (too strong locking) | 5'-GCGGCGTCACTATrAGGAAGATCCAATGTAC AGTATTGGATCTGAAGTAGCGCCGCCGTATAGTG ACGCCGC-3' (SEQ ID NO: 2) |
| ON→ON switch (too weak locking) | 5'-AAGACAATrAGGAAGACAATGTACAGTATTG TCTGAAGTAGCGCCGCCGTATTGTCTTC-3' (SEQ ID NO: 3) |

Table 2 below shows the DNA sequences (5'→3') of the ON→OFF switches among the lead ion-start switches comprising the unlocking module according to the present invention. In Table 2, rA signifies an RNA nucleotide.

TABLE 2

| Name | DNA sequence (5'→3') |
| --- | --- |
| ON→OFF switch (optimal unlocking) | 5'-CTGTACATTGTrAGGAAGAGCTTTGCTCTGA AGTAGCGCCGCCGTACAATGTACAGTATTGTAC G-3' (SEQ ID NO: 4) |
| OFF→OFF switch (too weak unlocking) | 5'-CTGTACATTACTrAGGAAGAGCTTTGCTCTG AAGTAGCGCCGCCGTAGTAATGTACAGTATTACT ACG-3' (SEQ ID NO: 5) |
| ON→ON switch (too strong unlocking) | 5'-CGTAATACTGTACATTrAGGAAGAGCTTTGC TCTGAAGTAGCGCCGCCGTAATGTACAGTATTAC G-3' (SEQ ID NO: 6) |

For optimal construction of the lead ion-start switch, the present inventors evaluated the melting temperature ($T_m$) and Gibbs free energy change ($\Delta G$) of each designed molecular switch before and after $Pb^{2+}$-triggered cleavage under isothermal amplification conditions. In consideration of $\Delta G$ between ON and OFF states, the optimal OFF→ON switch (FIG. 1b, left) was constructed to be 69 nucleotides (nts) in length (SEQ ID NO: 1). In the absence of $Pb^{2+}$, the secondary structure of the switch includes the well-folded binding module that yields a $T_m$ of 56.4° C. As the stem of TQ30 aptamer is stably locked, the active formation of the aptamer structure is assured at room temperature. In the presence of $Pb^{2+}$, the linkage between the locking module and the binding module should be cleaved, and a 9-nt strand, a part of the locking module, is subsequently released due to its low $T_m$ (26.6° C.). As a result, the binding module becomes destabilized, and the TQ30 aptamer cannot maintain the stem-loop structure, thereby losing the ability to inhibit the DNA polymerase.

The 64-nt-long ON→OFF switch (FIG. 1b, right), of which $T_m$ is 51.7° C., utilizes the unlocking module which forces the TQ30 aptamer's structural folding to be unlocked. However, due to $Pb^{2+}$-triggered RNA cleavage, this ON→OFF switch can also release an 11-nt short strand. As a result, the unlocking module is denatured, and instead, the binding module is folded in an active form, inhibiting the DNA polymerase.

FIG. 1a shows the structure and operating principle of the lead ion-start DNA polymerase switches according to one embodiment the present invention. The lead ion-start DNA polymerase switch according to the present invention is composed of: a binding module for DNA polymerase inhibition; a catalytic module for $Pb^{2+}$-responsive strand cleavage; and a locking or unlocking module for correlating the binding and catalytic modules.

Before $Pb^{2+}$ addition, the locking module induces the stem-loop structure of the binding module to be fully locked, inhibiting the isothermal amplification of DNA polymerase (OFF state). However, $Pb^{2+}$-triggered strand cleavage by the catalytic module can cause denaturing of the binding module, making the liberated DNA polymerase active for target amplicon production (ON state). The unlocking module that prevents the structural folding of the binding module is disabled upon $Pb^{2+}$ addition, switching the activity of DNA polymerase from ON to OFF (left).

FIG. 1b shows modular designs of the lead ion-start DNA polymerase switches according to the present invention. For the OFF→ON switch (left), $Pb^{2+}$-triggered catalytic RNA cleavage disables the locking module, liberating the DNA polymerase to be active. On the other hand, the ON→OFF switch (right) correlates the $Pb^{2+}$-triggered RNA cleavage with the aptamer refolding, suspending the isothermal polymerization (right).

The present invention is characterized by systematically integrating the TQ30 aptamer module functioning to inhibit DNA polymerase with the $Pb^{2+}$-start, RNA-cleaving GR5 DNAzyme module. In particular, relying on the type of interconnector that correlates the two modules with each other, $Pb^{2+}$ may serve as an initiator or a terminator of isothermal DNA amplification. The lead ion-start molecular switch constructed as described above may be specific to lead ions among various metal ions, and may dramatically increase the enzymatic activity of DNA polymerase (>25 times).

Another embodiment of the present invention provides a composition for isothermal polymerase amplification containing the metal ion-start DNA polymerase switch and a DNA polymerase.

Still another embodiment of the present invention provides an isothermal amplification method comprising steps of: preparing a mixture by mixing the metal ion-start DNA polymerase switch, metal ions, and a sample to be analyzed, and heating and incubating the mixture; preparing a composition for isothermal polymerase amplification by adding a DNA polymerase to the incubated mixture, followed by incubation; and isothermally amplifying a target gene using a mixture obtained by mixing a solution containing target gene-start primers and a template with the composition for isothermal polymerase amplification.

Hereinafter, the present invention will be described in detail with reference to Examples and Experimental Examples, but the scope of the present invention is not limited by these Examples.

I. Material and Methods

1. Reagents and Materials

DNA oligonucleotides used herein were synthesized by Bioneer Co. (Daejeon, Korea) and Integrated DNA Technologies, Inc. (Coralville, USA). The oligonucleotide sequences are listed in Table 3 below. *Thermus aquaticus* DNA polymerase (Taq DNA polymerase) was bought from New England Biolabs (Massachusetts, USA). Human Serum was purchased from Sigma-Aldrich, Inc. (St. Louis, US). Ethylenediaminetetraacetic acid (EDTA, pH 7.4) was bought from T&I Biotechnology (Hebei, China).

was heated at 90° C. for 5 min, cooled slowly to 25° C. (0.1° C./s) and incubated at 25° C. for 20 min. Part A and B were mixed together and incubated at 25° C. for 2 h. To immediately quench the reaction, 2 μL of 0.5 M EDTA was added.

3. Denaturing Urea Polyacrylamide Gel Electrophoresis (Urea PAGE)

13 μL of the final reacted solution was mixed with 6× loading buffer (5 μL) and 8 M urea (7 μL) for efficient loading, and subjected to electrophoresis analysis on a 10% urea-polyacrylamide gel. The analysis was carried out in 1× TBE (89 mM Tris, 89 mM borate, and 2 mM EDTA, pH 8.3) at 300 V for 25 min. The gel image was taken using Azure Gel Imaging System and the band intensities were quantified through a Gel Analyzer software.

4. Estimation of Thermodynamic Values and Secondary Structures

To obtain the calculated thermodynamic values and the predicted secondary structures of the designed molecular switches, the present inventors utilized the IDT OligoAnalyzer Tool.

TABLE 3

| Name | DNA Sequence (5'→3') |
|---|---|
| OFF→ON system | |
| OFF→ON switch (optimal locking) | GAGTCCAATrAGGAAGAGTCCAATGTACAGTATTGGACTCTGAAGTAGCGCCGCCGTATTGGACTCTTCC (Seq. No. 1) |
| OFF→OFF switch (too strong locking) | GCGGCGTCACTATrAGGAAGATCCAATGTACAGTATTGGATCTGAAGTAGCGCCGCCGTATAGTGACGCCGC (Seq. No. 2) |
| ON-ON switch (too weak locking) | AAGACAATrAGGAAGACAATGTACAGTATTGTCTGAAGTAGCGCCGCCGTATTGTCTTC (Seq. No. 3) |
| ON→OFF system | |
| ON→OFF switch (optimal unlocking) | CTGTACATTGTrAGGAAGAGCTTTGCTCTGAAGTAGCGCCGCCGTACAATGTACAGTATTGTACG (Seq. No. 4) |
| OFF→OFF switch (too weak unlocking) | CTGTACATTACTrAGGAAGAGCTTTGCTCTGAAGTAGCGCCGCCGTAGTAATGTACAGTATTACTACG (Seq. No. 5) |
| ON→ON switch (too strong unlocking) | CGTAATACTGTACATTrAGGAAGAGCTTTGCTCTGAAGTAGCGCCGCCGTAATGTACAGTATTACG (Seq. No. 6) |
| DNA templates and primers | |
| Template | CAGAAATCTCAGGGACTCTAAAGCTCAACTTGCATAAACTTCTGAGGA |
| FAM-primer | FAM-TCCTCAGAAGTTTATGCA |
| COVID template | CACATTGGCACCCGCAATCCTGCTAACAATGCTGCAATCGTGCTACAACT |
| COVID primer | AGTTGTAGCACGATTGCAGC |
| COVID FAM-primer | FAM-AGTTGTAGCACGATTGCAGC |

2. General Reaction Conditions

The reaction mixtures were separately prepared as part A and part B. Part A (total volume of 25 μL) was composed of 1× Taq reaction buffer (10 mM Tris-HCl, 50 mM KCl, 1.5 mM MgCl$_2$, pH 8.3), 500 μM dNTPs, 1 μM DNAzymatic switch, and 20 μM PbCl$_2$. The sample mixture was heated at 90° C. for 5 min, cooled slowly to 25° C. (0.1° C./s) and incubated at 25° C. for more than 2 h. Taq DNA polymerase (22 nM) was then added to the mixture and incubated for 20 min. Part B (total volume of 25 μL), composed of 1× Taq reaction buffer, 150 nM template, and 100 nM FAM-primer, 5. Reaction Conditions at Complex Bioanalytes (Human Serum and Saliva)

Overall experimental procedures followed the general reaction conditions. However, in preparation of part A, 10% human serum or 8% human saliva was additionally mixed with the existing components. Instead of using normal primer/template, COVID-19 nucleocapsid protein (N-protein) gene-based primer/template was used to prepare part B. After the reaction was quenched by EDTA, the product was stained with SYBR Green dye for 6 minutes and the fluorescence signal was detected through the Tecan Spark™

10M. For in-field analysis, the reaction product was irradiated with a portable UV lamp to take a picture with a mobile phone. The intensity of the obtained picture was quantitatively evaluated through ImageJ, an image analyzing software.

II. Results and Discussions

1. Characterization of $Pb^{2+}$-Specific DNA Polymerase Switches

In the OFF→ON switch, the $Pb^{2+}$-triggered activity change of DNA polymerase was evaluated by comparing the amounts of target amplicons resulting from isothermal polymerization, and the results of the evaluation are shown in FIGS. 2a-2d. The present inventors isothermally incubated the lead ion-start switches with FAM-labelled primers and DNA templates for 2 hours, and the reactions were immediately terminated by addition of ethylenediaminetetraacetic acid (EDTA), a metal ion chelating agent (see Table 3).

Figure 2A:
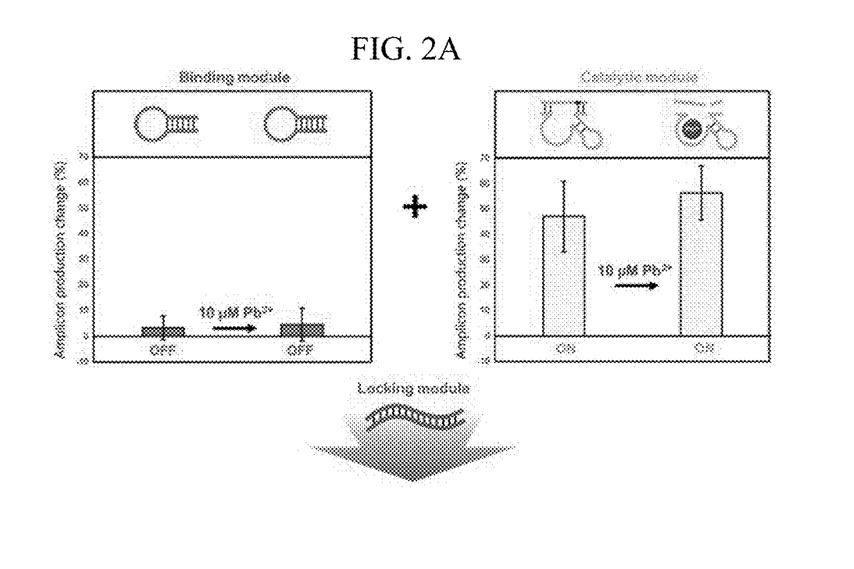
FIGS. 2a-2d show the results of evaluating the lead ion ($Pb^{2+}$)-triggered activity change of DNA polymerase for the OFF→ON switch by comparing the amounts of target amplicons resulting from isothermal polymerization.

The TQ30 aptamer completely inhibited the activity of DNA polymerase, and the inhibition efficiency thereof showed no significant difference between with and without $Pb^{2+}$ (FIG. 2a, left). The GR5 DNAzyme that contains several double-stranded stem domains somehow affected the primer extension of DNA polymerases (FIG. 2a, right). Compared to DNA polymerases only, addition of the GR5 DNAzyme caused to produce half the amount of target amplicons. The relevant mechanism is not clear, but some stem domains within the GR5 DNAzyme may be able to be recognized by the double strand DNA (dsDNA)-binding polymerases, thereby reducing the turnover rates in isothermal amplification (Breaker and Joyce 1994; Eom et al. 1996; Kim et al. 1995).

Figure 3:
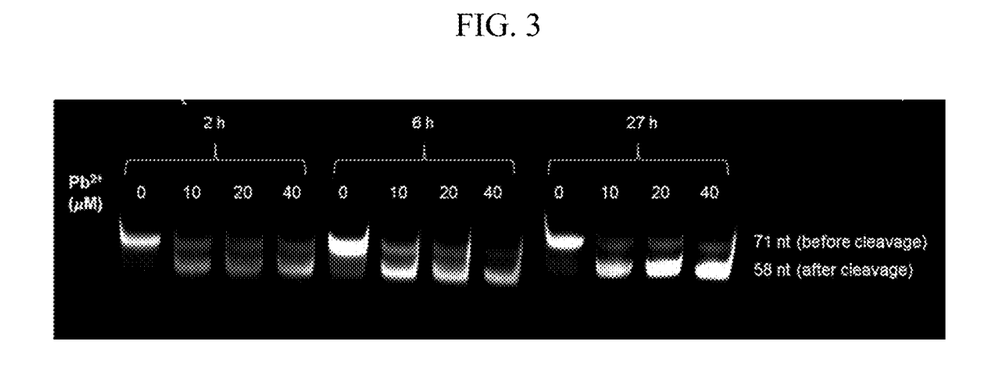
FIG. 3 shows the results of time-dependent cleavage of GR5 DNAzyme depending on the lead ion ($Pb^{2+}$) concentration.

FIG. 3 shows the results by treating 71-nt-GR5 DNAzyme with each of 0, 10, 20 and 40 μM $Pb^{2+}$ and incubating the treated DNAzymes for 2 hours, 6 hours and 27 hours, followed by PAGE analysis. When RNA cleavage occurs, the GR5 DNAzyme module may be split into 58-nt and 13-nt, which can be clearly distinguished by PAGE. The GR5 DNAzyme module exhibited a high cleavage rate by cleaving 71.6% within only 2 hours after addition of 10 μM $Pb^{2+}$.

That is, in the presence of 10 μM $Pb^{2+}$, the activity of DNA polymerase increased to a certain degree, which might be caused by the collapse of stems as a result of $Pb^{2+}$-triggered strand cleavage.

Figure 4:
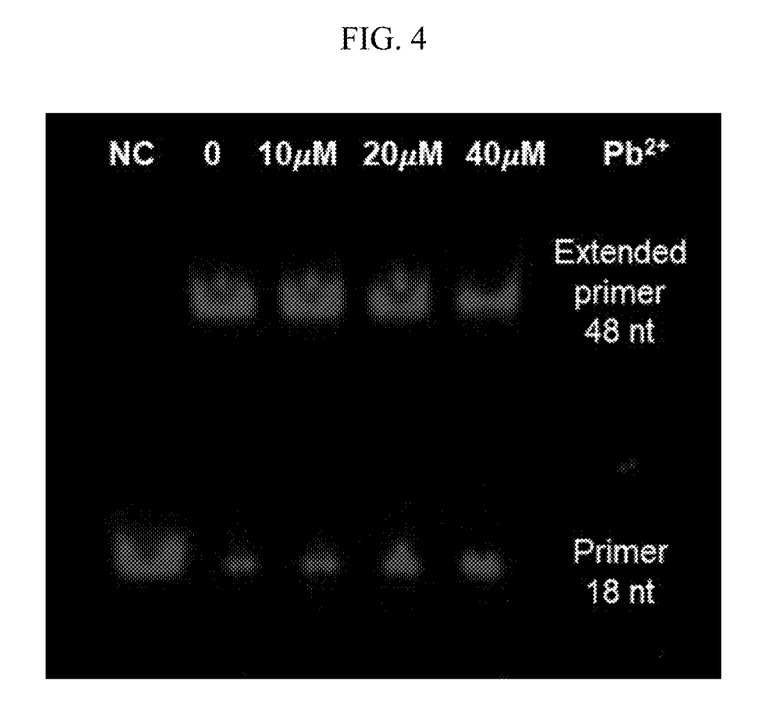
FIG. 4 shows the effect of lead ions ($Pb^{2+}$) on Taq DNA polymerase.

FIG. 4 shows the effect of $Pb^{2+}$ on Taq DNA polymerase. To test whether $Pb^{2+}$ itself could interfere with the native enzymatic activity of Taq DNA polymerase, various concentrations of $Pb^{2+}$ were added to the polymerase and the amount of extended primer was quantified. Compared to the polymerase activity in the absence of $Pb^{2+}$, the addition of 10 μM $Pb^{2+}$ did not change the ability of the polymerase to extend the primer. However, the addition of 20 μM or 40 μM of $Pb^{2+}$ slightly decreased the total amount of extended primer, indicating that the inhibition of polymerase activity was somewhat weak. For this reason, in the present invention, it was decided to use 10 μM (final concentration) of $Pb^{2+}$ to induce the response of the molecular switch. That is, $Pb^{2+}$ itself does not affect the activity of Taq polymerases, but >40 μM $Pb^{2+}$ was found to slightly influence the isothermal amplification of DNA polymerases (FIG. 4).

Figure 2B:
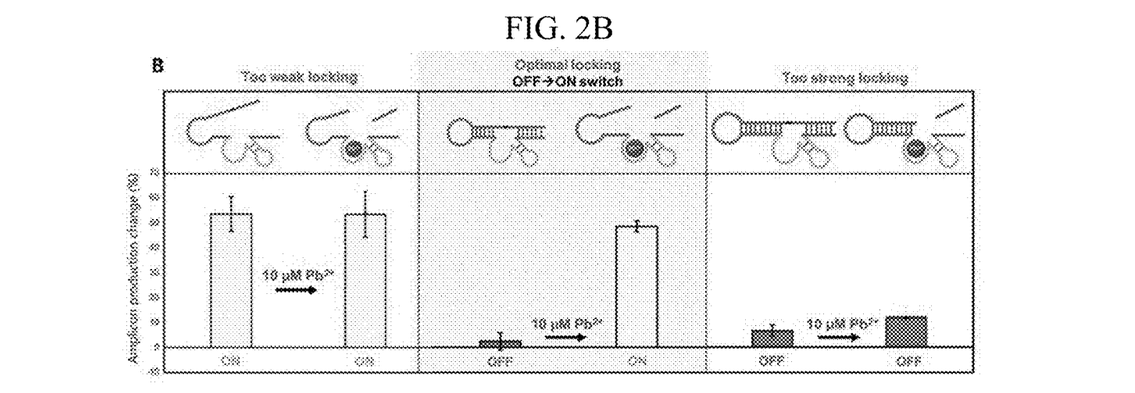

To achieve $Pb^{2+}$-induced polymerase activation, the TQ30 aptamer within the OFF→ON switch should bind to a DNA polymerase only in the absence of $Pb^{2+}$ (FIG. 2b, middle). As structural stabilization of the hairpin-shaped aptamer is influenced by the net hybridization energy of the two stems in the binding module and the locking module, their length adjustment was inevitably necessary (FIG. 1b, left). For instance, when short stems were included into the binding and locking modules (5'-AGACAATG-3'/5'-TATTGTCT-3' and 5'-AAGACAAT-3'/5'-ATTGTCTT-3', respectively), the net hybridization energy was too weak ($\Delta G=-21.72$ kcal $mol^{-1}$), thereby disabling the binding module even before $Pb^{2+}$ addition (FIG. 2b, left). In contrast, when the net hybridization energy of the long stems in the binding and locking modules (5'-AGATCCAATG-3'/5'-TATTGGATCT-3' and 5'-GCGGCGTCACTAT-3'/5'-ATAGTGACGCCGC-3', respectively) was too strong ($\Delta G=-41.48$ kcal $mol^{-1}$), the DNA polymerase inhibition activity of the TQ30 aptamer was unnecessarily maintained even after destabilization of the locking module in the presence of $Pb^{2+}$ (FIG. 2b, right). Meanwhile, the OFF→ON switch according to the present invention was optimal when the net hybridization energy of the two stems in the binding and locking modules (5'-AGAGTCCAATG-3'/5'-TATTGGACTCT-3' and 5'-GAGTCCAAT-3'/5'-ATTGGACTC-3, respectively) was $-30.66$ kcal $mol^{-1}$ (FIG. 2b, middle).

Figure 5:
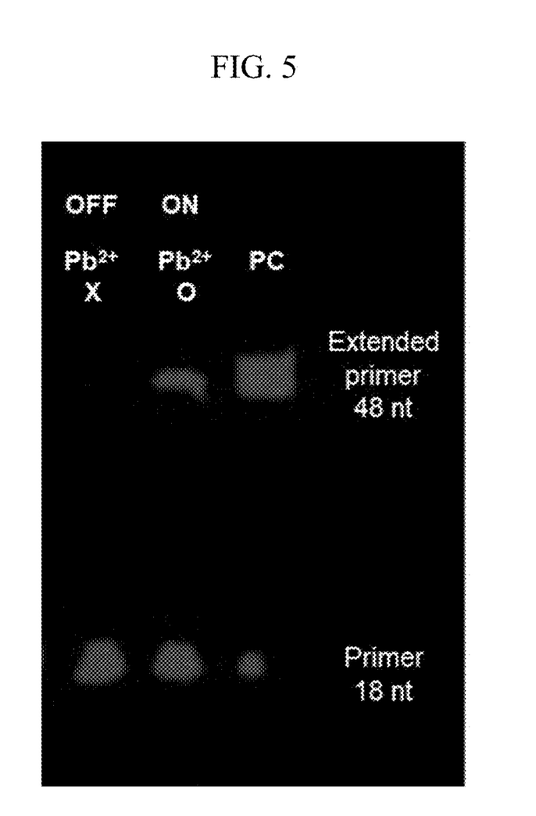
FIG. 5 shows the results of operation of the OFF→ON switch upon $Pb^{2+}$ addition.

The optimized switch of the present invention regulated the DNA polymerase to produce a negligible amount of target amplicons without $Pb^{2+}$ (>2% of the maximal production), but their target amplicon production dramatically increased in the presence of $Pb^{2+}$, yielding 25 times larger amplicons (FIG. 5).

FIG. 5 shows the results of operation of the OFF→ON switch upon $Pb^{2+}$ addition. The performance of the OFF→ON switch was tested by quantitatively comparing the amount of amplified FAM-primer between before and after addition of $Pb^{2+}$. A positive control (PC) was set as the percentage of FAM-primer amplified in the absence of the OFF→ON switch, and the relative band intensity in each condition was calculated to derive amplicon production change (%). In the presence of the OFF→ON switch, the signal change significantly increased from 2.45% (OFF) to 48.74% (ON) upon addition of 10 μM $Pb^{2+}$. This means that the switch properly operated to restore the activity of DNA polymerase activity.

Figure 2C:
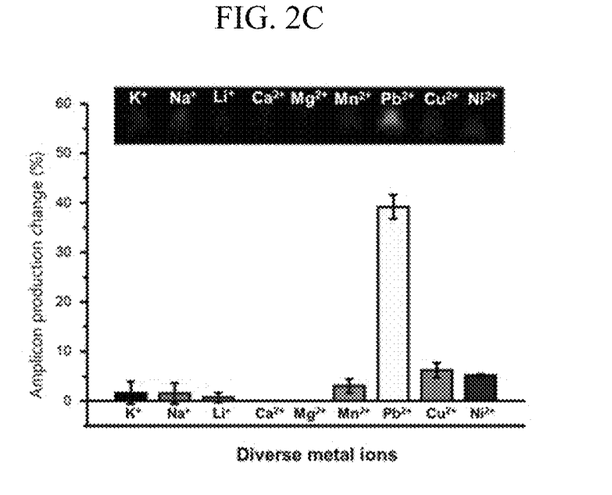
Figure 2D:
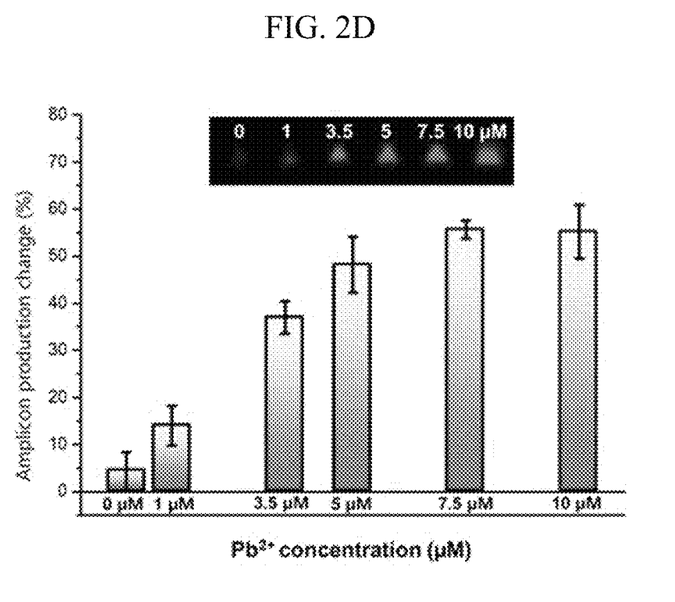

Importantly, the OFF→ON switch was highly $Pb^{2+}$-start in activating DNA polymerases. To evaluate the metal ion dependence, the present inventors incubated the optimal OFF→ON switch of the present invention with various metal ions ($K^+$, $Na^+$, $Li^+$, $Ca^{2+}$, $Mg^{2+}$, $Mn^{2+}$, $Pb^{2+}$, $Cu^{2+}$, and $Ni^{2+}$) (FIG. 2c). As a result, it was confirmed that only $Pb^{2+}$ ions were effective to recover the activity of DNA polymerases. When other metal ions were introduced, there was no significant change in production of target amplicons, assuring high $Pb^{2+}$ selectivity of the lead-start switch. This is mainly attributed to the exceptionally high selectivity to $Pb^{2+}$ for the catalytic cleavage of substrates by GR5 DNAzymes, which also proves that $Pb^{2+}$-triggered cleavage is indeed the key process to activate the DNA polymerase. Moreover, as the activity of GR5 DNAzyme is synchronized with that of DNA polymerase, the DNAzymatic OFF→ON switch of the present invention can control the degree of polymerization activity by varying the concentrations of $Pb^{2+}$ (FIG. 2d). In particular, the amplicon production changes as a result of isothermal amplification were proportional to a $Pb^{2+}$ concentration ranging from 0 to 5 μM.

Figure 6:
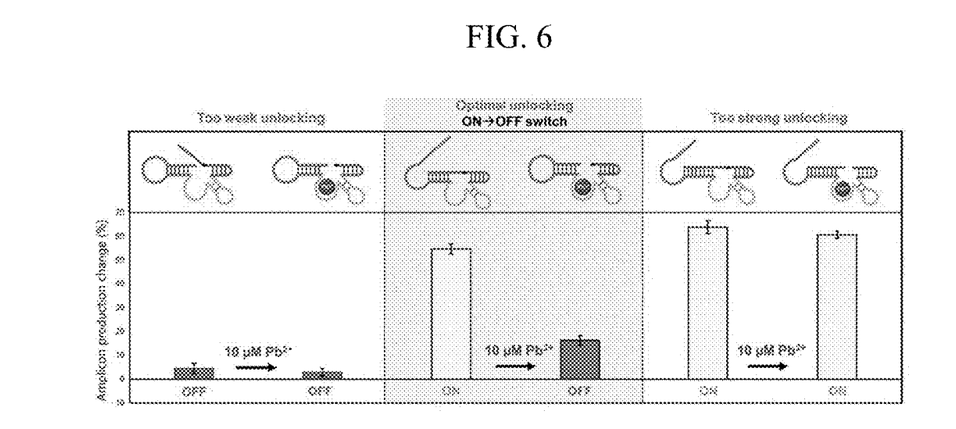
FIG. 6 shows that, mediated by the unlocking module, the optimal ON→OFF switch changes the activity state of DNA polymerase from ON to OFF by responding to lead ions ($Pb^{2+}$).
Figure 7:
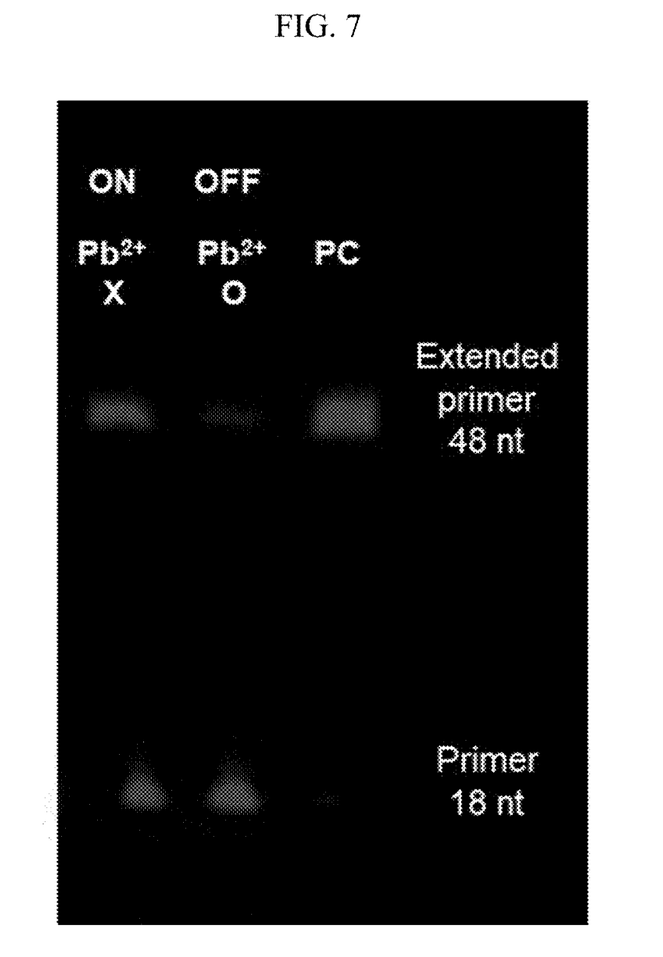
FIG. 7 shows the results of operation of the ON→OFF switch upon $Pb^{2+}$ addition.

FIG. 6 shows that, mediated by the unlocking module, the optimized ON→OFF switch changes the activity state of DNA polymerase from ON to OFF by responding to $Pb^{2+}$. When the unlocking module is chosen to interconnect between the binding module and the catalytic module, the resulting DNAzymatic switch responds to $Pb^{2+}$ by changing the activity state of DNA polymerase from ON to OFF. At this moment, the hybridization competition between the binding module and the unlocking module was critical. When the stabilization energy of the interconnecting stem was either too high or low (e.g., −9.33 kcal mol$^{-1}$ for 5'-TATTACG-3'/5'-CGTAATG-3' or −13.24 kcal mol$^{-1}$ for 5'-TATTACTACG-3'/5'-CGTAGTAATG-3'), there was no activity change of DNA polymerase, regardless of $Pb^{2+}$ addition (FIG. 6, left and right). Incorporation of the optimal stem (5'-TATTGTACG-3'/5'-CGTACAATG-3') with ΔG of −12.63 kcal mol$^{-1}$ eventually allowed the formation of ON→OFF switch, achieving $Pb^{2+}$-induced polymerase deactivation (see FIG. 6, middle and FIG. 7).

2. Quantitative and Parallel Gene Detection in Complex Bioanalytes

Figure 8A:
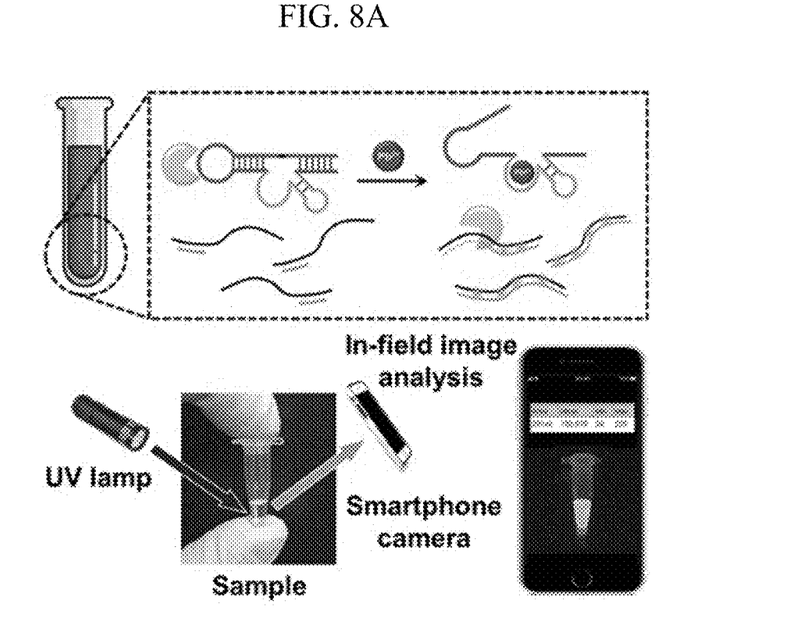
FIGS. 8a-8c show a process of performing quantitative analysis of multiple samples in complex mixtures using the metal ion-start DNA polymerase switch as an isothermal amplification controller and the results of the quantitative analysis.

The lead-start DNA polymerase switch of the present invention can serve as an excellent isothermal amplification controller, allowing PoC tests to be performed in a parallel and quantitative manner. Inherently, the isothermal amplification guarantees significantly high sensitivity and reliability in analyte detection even if the target analytes exist in complex mixtures, such as human serum or saliva (Calvert et al. 2017). During the sensitive and reliable isothermal amplification, the lead-start switches of the present invention can precisely control a number of reactions to be initiated and terminated at the same time, avoiding nonspecific amplification. All the reactions can be prepared individually, but they are isothermally amplified under the identical conditions, allowing quantitative and reproducible analysis of all the amplicons. It is well known that there are many ways to easily and simply visualize the amplified dsDNAs, and for example, SYBR Green dye's selective intercalation into dsDNAs can be used for fluorescence-based naked eye detection (Noble and Fuhrman 1998). To actualize the in-field fluorescent detection, the present inventors performed the isothermal amplification of multiple samples simultaneously, and using a portable UV lamp and a smartphone, the fluorescent signals of the resulting amplicons were obtained and subsequently analyzed by the image analyzing mobile app (FIGS. 8a-8c).

Figure 8B:
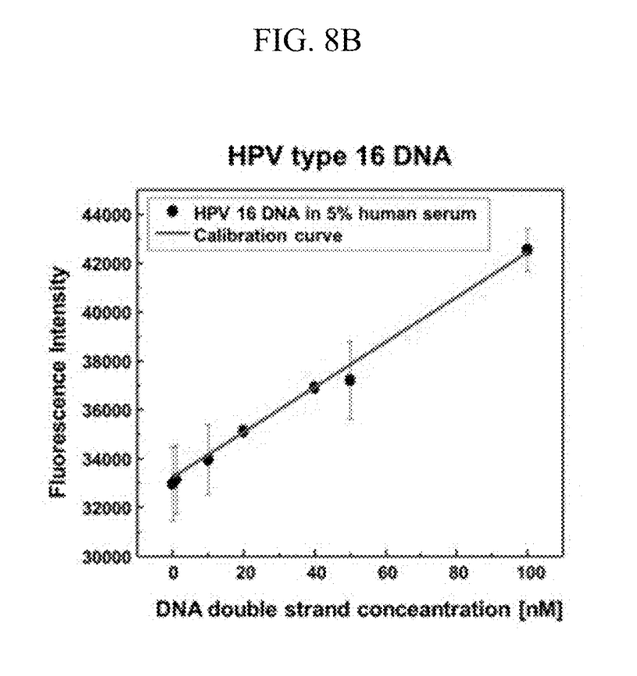

To validate the potential of the lead-start switch for on-demand isothermal amplification of multiple samples, the OFF→ON switch of the present invention was applied to detect the clinically important HPV type 16 DNA in human serum without an additional purification process (FIG. 8b). As the amount of HPV16 DNA is correlated with the occurrence of cervical cancer, which is one of the most common cause of death from cancer in women, its quantification with high sensitivity is necessary for the early diagnosis of HPV infections. Even though all the samples (>20 reactions) were prepared one by one, the initiation and termination of the isothermal reactions were synchronized by the addition of $Pb^2$ and EDTA, respectively. When various concentrations of HPV16 DNA ranging from 0.1 nM to 100 nM were investigated in diluted human serum, there was a strong linear relationship between the HPV16 DNA concentration and the dsDNA-specific fluorescence, yielding a linear correlation coefficient r>0.998. Currently, several biosensors for the determination of HPV type 16 DNA have been reported to detect the gene concentrations as low as 0.15 nM, which is comparable with 0.1 nM HPV16 DNA in the present invention, demonstrating the potential applicability of the lead-start isothermal amplification of the present invention in actual PoC tests (Iravani 2020; Song et al. 2021).

Figure 8C:
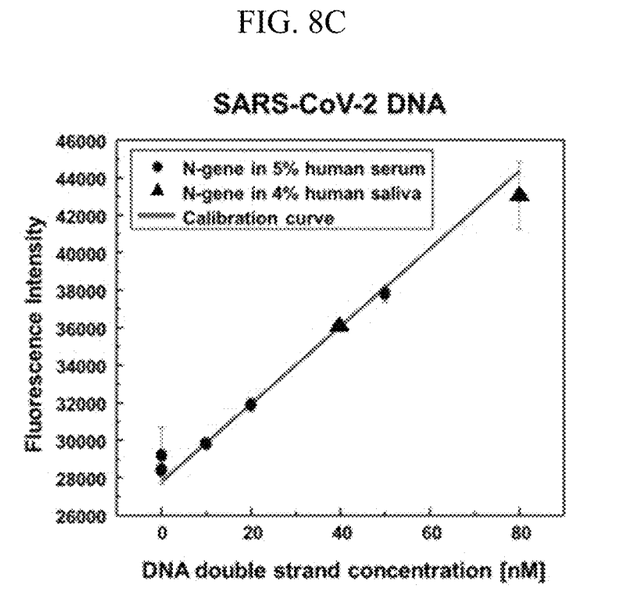

The DNAzymatic switch of the present invention can also be applicable for quantifying another type of target DNA with clinical significance, which is reverse-transcribed nucleocapsid protein (N-protein) gene of SARS-CoV-2 in human serum (FIG. 8c).

As DNA polymerases are known to tolerate compositional differences by the choice of clinical specimens, the present inventors quantitatively measured the concentrations of N-protein genes after reverse transcription in saliva, which is a representative type of specimens for the primary COVID-19 diagnostic method. The fluorescent signals of saliva samples were exactly fitted on the serum-based calibration curve (r>0.999), indicating the reliability and generality of the in-field gene detection technique of the present invention (Mullis et al. 1986; Nagai et al. 1998; Wyllie et al. 2020).

Therefore, the present invention provides a method of quantitatively analyzing a target gene using the metal ion-start DNA polymerase switch.

As lots of structure-switching aptamers targeting diverse metal ions and small molecules have been developed recently, their successful application to regulation of isothermal amplification could not only vary the trigger of reaction, but also make the reaction begin immediately (Fong et al. 2016; Oh et al. 2010; Oh et al. 2013; Qu et al. 2016). In addition, to be compatible with a variety of isothermal amplification techniques, the molecular switches of the present invention are necessary to be further tailored for regulating other types of DNA polymerases, which can be also benefited by in vitro selection technology (Gening et al. 2006; Li and Macdonald 2015; Mori et al. 2012; Ohuchi et al. 2012; Zhao et al. 2015). Given the availability of various polymerase-binding aptamers, the current state-of-art isothermal amplification techniques, including RCA and LAMP, would be further upgraded to be used even in quantitative and parallel manner.

REFERENCES

1. W. Coleman and G. Tsongalis, Diagn. Mol. Pathol., 2017, 15-23.
2. K. A. Eckert and T. A. Kunkel, Genome Res., 1991, 1, 17-24.
3. M. F. Kramer and D. M. Coen, Curr. Protoc. Mol. Biol., 2001, 56, 15.
4. Q. Chou, M. Russell, D. E. Birch, J. Raymond and W. Bloch, Nucleic Acids Res., 1992, 20, 1717-1723.
5. S. A. Bustin and T. Nolan, J. Biomol. Tech., 2004, 15, 155.
6. N. Paul, J. Shum and T. Le, RT-PCR Protocols, 2010, 301-318.
7. M. R. Green and J. Sambrook, Cold Spring Harbor Protocols, 2018, 2018, pdb. prot095125.
8. D. E. Birch, L. Kolmodin, J. Wong, G. Zangenberg, M. Zoccoli, N. McKinney and K. Young, Nature, 1996, 381, 445-446.
9. D. J. Sharkey, E. R. Scalice, K. G. Christy, S. M. Atwood and J. L. Daiss, Nat. Biotechnol., 1994, 12, 506-509.
10. E. R. Scalice, D. J. Sharkey and J. L. Daiss, J. Immunol. Methods., 1994, 172, 147-163.
11. C. Dang and S. D. Jayasena, J. Mol. Biol., 1996, 264, 268-278.
12. Y. Lin and S. D. Jayasena, J. Mol. Biol., 1997, 271, 100-111.
13. V. Marx, Nat. Methods., 2015, 12, 393-397.
14. P. L. Lee, Mol. Ecol. Resour., 2017, 17, 138.

15. K. Hsieh, A. S. Patterson, B. S. Ferguson, K. W. Plaxco and H. T. Soh, Angew. Chem., Int. Ed., 2012, 51, 4896-4900.
16. J. Song, M. G. Mauk, B. A. Hackett, S. Cherry, H. H. Bau and C. Liu, Anal. Chem., 2016, 88, 7289-7294.
17. K. S. Park, C. Y. Lee and H. G. Park, Chem. Commun., 2015, 51, 9942-9945.
18. K. S. Park, C. Y. Lee and H. G. Park, Chem. Commun., 2016, 52, 4868-4871.
19. N. R. Ho, G. S. Lim, N. R. Sundah, D. Lim, T. P. Loh and H. Shao, Nat. Commun., 2018, 9, 1-11.
20. K. S. Park, C.-H. Huang, K. Lee, Y.-E. Yoo, C. M. Castro, R. Weissleder and H. Lee, Sci. Adv., 2016, 2, e1600300.
21. R. Saran and J. Liu, Inorg. Chem. Front., 2016, 3, 494-501.
22. R. R. Breaker and G. F. Joyce, Chem. Biol., 1994, 1, 223-229.
23. S. H. Eom, J. Wang and T. A. Steitz, Nature, 1996, 382, 278-281.
24. Y. Kim, S. H. Eom, J. Wang, D.-S. Lee, S. W. Suh and T. A. Steitz, Nature, 1995, 376, 612-616.
25. A. E. Calvert, B. J. Biggerstaff, N. A. Tanner, M. Lauterbach and R. S. Lanciotti, PloS one, 2017, 12, e0185340.
26. R. T. Noble and J. A. Fuhrman, Aquat. Microb. Ecol., 1998, 14, 113-118.
27. J. Cuzick, G. Terry, L. Ho, T. Hollingworth and M. Anderson, Lancet, 1992, 339, 959-960.
28. S. Jampasa, W. Siangproh, R. Laocharoensuk, P. Yanatatsaneejit, T. Vilaivan and O. Chailapakul, Sens. Actuators B Chem., 2018, 265, 514-521.
29. J. R. Espinosa, M. Galván, A. S. Quiñones, J. L. Ayala, V. Ávila and S. M. Durón, Molecules, 2021, 26, 3436.
30. M. Nagai, A. Yoshida and N. Sato, IUBMB Life, 1998, 44, 157-163.
31. K. Mullis, F. Faloona, S. Scharf, R. Saiki, G. Horn and H. Erlich, Cold Spring Harb. Symp. Quant. Biol., 1986, 263-273.
32. A. L. Wyllie, J. Fournier, A. Casanovas-Massana, M. Campbell, M. Tokuyama, P. Vijayakumar, J. L. Warren, B. Geng, M. C. Muenker and A. J. Moore, N. Engl. J. Med., 2020, 383, 1283-1286.
33. B. S. Ferguson, D. A. Hoggarth, D. Maliniak, K. Ploense, R. J. White, N. Woodward, K. Hsieh, A. J. Bonham, M. Eisenstein and T. E. Kippin, Sci. Transl. Med., 2013, 5, 213ra165-213ra165.
34. R. Nutiu and Y. Li, J. Am. Chem. Soc., 2003, 125, 4771-4778.
35. H. Qu, A. T. Csordas, J. Wang, S. S. Oh, M. S. Eisenstein and H. T. Soh, ACS Nano, 2016, 10, 7558-7565.
36. S. S. Oh, K. Plakos, X. Lou, Y. Xiao and H. T. Soh, Proc. Natl. Acad. Sci. U.S.A., 2010, 107, 14053-14058.
37. S. S. Oh, K. Plakos, Y. Xiao, M. Eisenstein and H. T. Soh, ACS Nano, 2013, 7, 9675-9683.
38. F. Y. Fong, S. S. Oh, C. J. Hawker and H. T. Soh, Angew. Chem., Int. Ed., 2016, 55, 15258-15262.
39. Y. Zhao, F. Chen, Q. Li, L. Wang and C. Fan, Chem. Rev., 2015, 115, 12491-12545.
40. J. Li and J. Macdonald, Biosens. Bioelectron., 2015, 64, 196-211.
41. Y. Mori, Y. Nakamura and S. Ohuchi, Biochem. Biophys. Res. Commun., 2012, 420, 440-443.
42. L. V. Gening, S. A. Klincheva, A. Reshetnjak, A. P. Grollman and H. Miller, Nucleic Acids Res., 2006, 34, 2579-2586.
43. S. Ohuchi, Y. Mori and Y. Nakamura, FEBS open bio, 2012, 2, 203-207.

What is claimed is:

1. A metal ion-start DNA polymerase switch comprising:
a binding module composed of an aptamer for inhibiting DNA polymerase activity;
a locking or unlocking module; and
a catalytic module connecting between the binding module and the locking or unlocking module and composed of DNAzyme with a metal-ion recognition site,
wherein the aptamer comprises consensus sequence motif of TQ30, which is composed of a fixed loop that directly contacts a DNA polymerase, and a programmable stem that serves as a binding stabilizer,
wherein the metal ion-start DNA polymerase switch comprising the locking module comprises the nucleic acid sequence of SEQ ID NO: 1, and the metal ion-start DNA polymerase switch comprising the unlocking module comprises the nucleic acid sequence of SEQ ID NO: 4,
wherein the DNAzyme is $Pb2^+$-responsive and RNA-cleaving GR5 DNAzyme, and
wherein the DNA polymerase is Taq polymerase.

2. A composition for isothermal polymerase amplification containing: the metal ion-start DNA polymerase switch of claim 1; and a DNA polymerase,
wherein the DNA polymerase is Tag polymerase.

3. The composition of claim 2, wherein the locking module is cleaved by the DNAzyme to activate the DNA polymerase upon the addition of Pb2+ ions.

4. The composition of claim 2, wherein the unlocking module is configured to deactivate the DNA polymerase in the presence of Pb2+ ions.

5. A method for quantitative analysis of a target gene comprising steps of: preparing a mixture by mixing the metal ion-start DNA polymerase switch according to claim 1, Pb2+ ions, and a sample to be analyzed, and heating and incubating the mixture; and quantifying an amount of the target gene in the sample.

* * * * *